United States Patent [19]

Ioffe

[11] Patent Number: 4,580,339
[45] Date of Patent: Apr. 8, 1986

[54] METHOD FOR FABRICATING A DISPOSABLE ELECTRODE FOR TRANSCUTANEOUS NERVE STIMULATOR

[75] Inventor: Zosim Ioffe, Saint Paul, Minn.
[73] Assignee: Empi, Inc., Fridley, Minn.
[21] Appl. No.: 642,487
[22] Filed: Aug. 20, 1984

Related U.S. Application Data

[62] Division of Ser. No. 405,506, Aug. 5, 1982, abandoned.
[51] Int. Cl.[4] .............................................. H01R 43/00
[52] U.S. Cl. ........................................ 29/825; 128/641
[58] Field of Search ........................ 128/639, 640, 641; 29/825, 874, 878

[56] References Cited

U.S. PATENT DOCUMENTS

| 3,805,769 | 4/1974 | Sessions | 29/825 X |
| 3,901,218 | 8/1975 | Buchalter | 128/641 |
| 3,972,329 | 8/1976 | Kaufman | 128/641 |
| 4,082,086 | 4/1978 | Page et al. | 29/831 X |
| 4,409,981 | 10/1983 | Lundberg | 128/640 |

Primary Examiner—Mark Rosenbaum
Assistant Examiner—Carl J. Arbes
Attorney, Agent, or Firm—Kinney & Lange

[57] ABSTRACT

A method for fabricating an integral disposal electrode for establishing a low impedance electrical connection to a patient's skin. A web of flexible electrically nonconductive adhesive tape, a web of flexible electrically conductive sheet material, a web of flexible biocompatible electrically conductive adhesive polymer material, and a web of nonadhesive protective material are provided and laminated together to form a composite web. The web of adhesive polymer material has a width at least essentially equal to a width of the conductive sheet material web, and less than a width of the nonconductive adhesive tape web. Electrical terminals are attached to the web of conductive sheet material at spaced longitudinal locations. Individual electrodes are formed by severing the laminated composite web in a transverse direction at positions between adjacent spaced electrical terminals.

3 Claims, 5 Drawing Figures

METHOD FOR FABRICATING A DISPOSABLE ELECTRODE FOR TRANSCUTANEOUS NERVE STIMULATOR

This is a division, of application Ser. No. 06/405,506, filed Aug. 5, 1982 now abandoned.

BACKGROUND OF THE INVENTION

1. Field of the Invention

The present invention relates to disposable medical electrodes for use with electromedical equipment which applies electrical stimulation through the patient's skin.

2. Description of the Prior Art

Medical electrodes which are attached to the skin of a patient have been used for many years. With the ever-increasing sophistication of medical electronics, medical electrodes are continually finding new and wider uses. One common type of medical electrode may be termed a "monitoring" electrode, which is used in conjunction with monitoring equipment such as electrocardiogram (EKG) and electroencephalograph (EEG) equipment. These monitoring electrodes are typically used in sensing voltages, and the current levels are quite low. Due to the low current density encountered, the area of electrical contact between the monitoring electrode and the patient's skin can be relatively small without danger of damage to the patient's skin.

A transmitting or stimulating electrode for use with a transcutaneous electrical nerve stimulator (TENS) device of similar electromedical equipment is used for the introduction of electrical current into the patient's body. Since the electrical currents applied are much larger than those encountered with monitoring electrodes, the stimulating electrode must provide a relatively large area of contact with the patient's skin so that the current density of the electrical current being applied is low enough that it does not damage skin tissue. This requires that the conductivity across the entire area of the electrode be relatively high, so as to distribute the current over a relatively large area of skin. In addition, local "hot spots" of nonuniform (higher) current density must be avoided.

In the case of a stimulating medical electrode used with TENS devices, the electrode is typically applied by the patient without the assistance of medical personnel. As a result, it is important that the electrode be very simple and convenient to use.

Since TENS devices are typically used for treatment of chronic or long term pain, the electrodes used with TENS devices must be capable of remaining on the patient's body for prolonged periods of time (several days or more). The electrode must adhere well to the patient's body despite normal physical movement and normal activities such as bathing.

In the past, reusable TENS electrodes have been widely used. These reusable electrodes normally require application of an electrically conductive gel or paste to ensure electrical contact between the electrode and the patient's skin.

Considerable effort has been devoted to the development of a disposable TENS electrode which can simply be discarded after a single use, and which is easier and more convenient to use than a reusable electrode. Because it is intended to be discarded after a single use, the disposable electrode should be of very low cost.

Unfortunately, the prior art disposable TENS electrodes have had several disadvantages. First, the disposable TENS electrodes typically have had a small electrically active area, which tends to cause high current densities through the patient's skin. This can result in a higher incidence of skin irritation.

Second, those prior art disposable TENS electrodes which are self-adhesive (i.e. the adhesive to the skin is an electrical conductor) have been less than satisfactory. The self-adhesive electrode typically is either eccessively aggressive and debrides the skin, or is non-tacky and tends to fall off the patient's skin. The development of an adhesive having the combination property of uniform consistent electrical conductivity over a significant surface area and a sufficiently tacky surface to hold the electrode on the patient's skin has proved to be an extremely difficult technical problem.

Third, the prior art disposable TENS electrodes have been expensive, due to complexity in manufacturing and high cost of materials. These high cost factors have been the result of the need to avoid hot spots and to provide a disposable electrode which has both excellent adhesive properties and high, uniform electrical conductivity.

Fourth, some prior art disposable electrodes have suffered from a lack of biocompatibility (skin irritation). These disposable electrodes have involved direct metal contact with the skin, or have used a foam soaked in a wet ionic conductor.

There is a continuing need for an improved electrode for use with TENS devices and other electromedical equipment which applies electrical current to the patient's body through the patient's skin. In particular, there is a need for an inexpensive disposable TENS electrode which is easily manufacturable, is easy and convenient to use without the assistance of medical personnel, and provides uniform current density so that the danger of skin irritation or damage is minimized.

SUMMARY OF THE INVENTION

The present invention is an integral disposable electrode which is applied to a patient's skin, and is used in conjunction with an electromedical apparatus for applying electrical signals to the patient's body. The integral disposable electrode includes a strip of electrically conductive adhesive hydrophylic polymer material, an electrically conductive sheet, an electrically nonconductive adhesive tape, and electrical terminal means.

The strip of electrically conductive adhesive polymer material is generally rectangular, with top and bottom surfaces, first and second opposite ends, and first and second opposite sides. The bottom surface of the strip is positioned to contact, conform to, and adhere to the patient's skin to provide an electrically conductive interface with the patient's skin. The adhesive properties of the conductive adhesive polymer material allow maintenance of intimate contact with the patient's skin, which is important to avoid hot spots. With the electrode of the present invention, however, the adhesive intimate contact between the electrically conductive adhesive polymer material and the patient's skin is not required to support the entire physical structure of the electrode. Instead, this is provided by the nonconductive adhesive tape.

The electrically conductive sheet, which is preferably a metal foil, overlies and is adhered to essentially the entire top surface of the conductive adhesive strip. The electrically conductive sheet provides a low, uniform current density over essentially the entire area of the conductive adhesive polymer strip.

The electrically nonconductive adhesive tape overlies the conductive sheet, and has a biocompatible nonconductive adhesive layer on its bottom surface. The tape provides structural support for the electrode, and also provides the adhesion necessary to attach the electrode to the patient's skin. The tape has a width which is greater than the width of the strip, so that first and second adhesive regions of the tape are formed adjacent to the first and second opposite sides of the conductive adhesive strip. These first and second adhesive regions have greater adhesion to the patient's skin than the adhesion of the conductive adhesive polymer strip.

The electrical terminal means, which in preferred embodiments is a snap connector, is attached to the electrically conductive sheet and extends through the nonconductive adhesive tape to permit electrical connection to the electrode.

In preferred embodiments of the present invention, a nonadhesive protective sheet covers the entire bottom surface of the electrode, and is attached to the electrode by the adhesion of both the nonconductive tape and the electrically conductive adhesive polymer material. When the patient wishes to use the disposable electrode, the protective sheet is removed, and the electrode is pressed against the skin of the patient at the desired position. The first and second adhesive regions of the nonconductive tape attach the electrode to the patient's skin. The strip of conductive adhesive hydrophylic polymer material also contacts and conforms to the surface of the patient's skin, and the adhesive properties of the conductive adhesive hydrophylic polymer strip ensure maintenance of a uniform, intimate contact with the patient's skin. Stimulating electrical signals are supplied through the electrical terminal means, are distributed by the electrically conductive sheet, and are applied by the conductive adhesive hydrophylic polymer strip to the patient's skin.

DETAILED DESCRIPTION OF THE PREFERRED EMBODIMENTS

Figure 1:
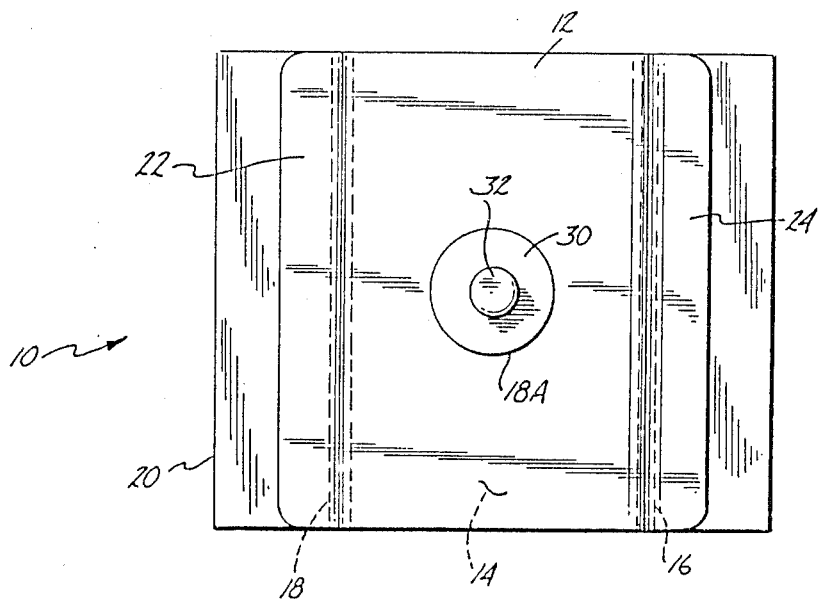
FIG. 1 is a top view of the disposable stimulating electrode of the present invention.
Figure 2:
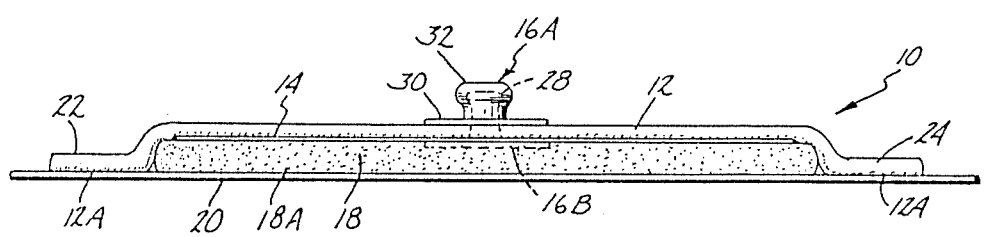
FIG. 2 is an end view of the disposable electrode.
Figure 3:
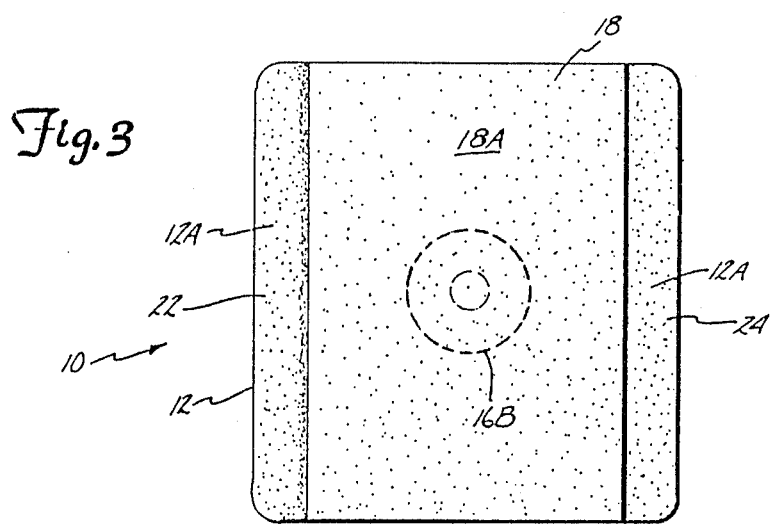
FIG. 3 is a bottom view of the disposable electrode, with a protective wax paper sheet removed from bottom adhesive surfaces of the electrode.

Stimulating electrode 10, which is shown in FIGS. 1-4, is a low cost, easily manufacturable, and convenient to use electrode which is used in conjunction with a TENS device, or other electromedical equipment which applies electrical current to a patient through the patient's skin. Electrode 10 is an integral, laminated structure which includes nonconductive adhesive tape 12, electrically conductive sheet 14, snap electrical connector 16, adhesive conductive polymer strip 18, and protective wax paper sheet 20.

Adhesive tape 12 serves as a structural support component of electrode 10, and also provides the means of attaching the electrode 10 to the patient's skin. As shown in FIGS. 1-4, adhesive tape 12 has essentially the same length as conductive sheet 14 and adhesive conductive polymer strip 18, but has a greater width. First and second adhesive regions 22 and 24 of adhesive tape 12 are positioned on opposite sides of adhesive conductive polymer 18. Lower surface 12A of adhesive tape 12 is a adhesive layer which adheres to the patient's skin, and holds electrode 10 in place reliably for prolonged periods of time (i.e., many days). Adhesive tape 10 is sufficiently flexible to conform to the patient's skin.

In a preferred embodiment of the present invention, adhesive tape 10 is a hypoallergenic adhesive nonconductive material such as a foam tape. One particularly advantageous adhesive foam tape is No. MED 632 manufactured by Fasson Corp. In the preferred embodiments shown in FIGS. 1-4, adhesive tape 12 has a width of about 35.0 millimeters, a length of about 40.0 millimeters, and a thickness of about 0.8 millimeters.

Conductive sheet 14 is preferably a metal foil (such as tin or stainless steel) which is in electrical contact with connector 18. Conductive sheet 14 provides a low and even current density in both lateral directions (i.e. width and length) over the entire top surface of adhesive conductive polymer 18. The thickness of conductive sheet 14 is very small (on the order of about 0.0762 millimeters) so that sheet 14 is pliable and is capable of conforming to the skin surface of the patient. In the preferred embodiment shown in FIGS. 1-4, conductive sheet 14 has a length of about 40.0 millimeters and a width of about 19.0 millimeters. Although in the embodiment shown in FIGS. 1-4 conductive sheet 14 is a solid metal foil, it can also take the form of a perforated foil, metal screen, wire mesh, or highly conductive cloth, so long as it is flexible and has high conductivity so as to provide low current density and even current distribution in both lateral directions.

Figure 4:
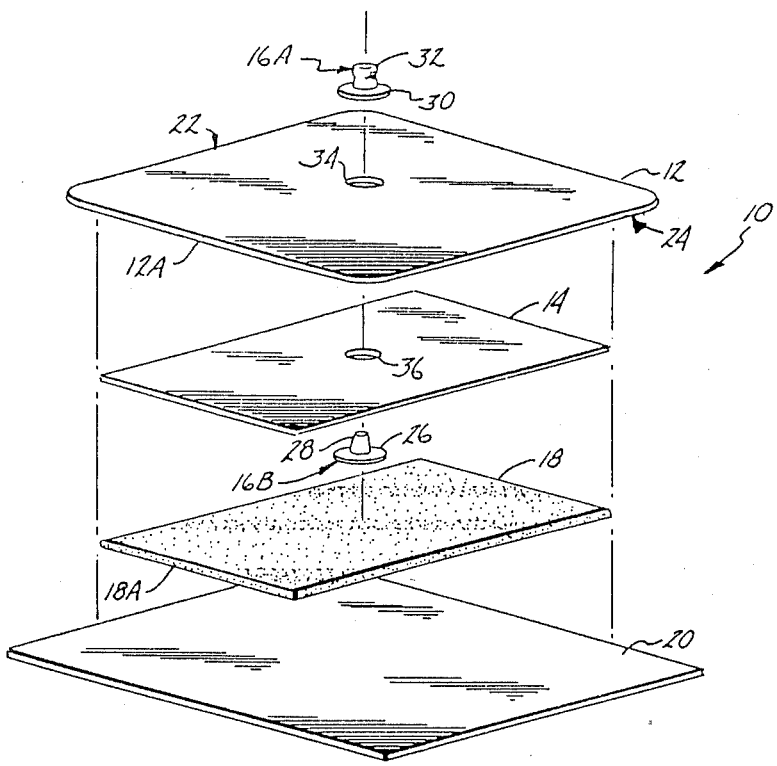
FIG. 4 is an exploded perspective view of the disposable electrode.

Snap connector 16 ensures reliable and flexible electrical connection between electrode 10 and the patient's TENS device lead wire (not shown) by means of a snap socket (not shown) which is at the end of the lead wire and which can be easily snapped into and out of engagement with snap connector 16. As shown in FIG. 4, snap connector 16 has a metal upper part 16A and a metal lower part 16B which are connected together. Lower part 16B has a base 26 and a stud 28 which extends upward through conductive sheet 14 and adhesive tape 12. Upper part 16A has a base 30 and a socket 32 which mates with stud 28. Socket 32 is crimped around stud 28 to hold upper and lower parts 16A and 16B together with tape 12 and sheet 14 between them. Snap connector 16 is positioned essentially at the center of conductive sheet 14 (and thus the center of electrode 10). In FIG. 4, a hole 34 is shown in tape 12 and a hole 36 is shown in conductive sheet 14. Holes 34 and 36 are preferably formed at the same time that upper and lower connector parts 16A and 16B preferably are joined together, without a separate hole punching operation. Upper and lower connector parts 16A and 16B can be joined together using a conventional rivet type snap connector forming apparatus.

Although snap connector 16 represents the preferred form of the electrical connector to conductive sheet 14, other forms of electrical connectors can be used. For example, in another embodiment a pigtail electrical connector is used. Snap connector 16 is preferred, however, because of the ease of assembly and the rugged integral structure which is achieved.

Adhesive conductive polymer 18 underlies conductive sheet 14, and provides electrical contact between conductive sheet 14 and the patient's skin. Adhesive conductive polymer strip 18 is a hydrophylic polymer having a high degree of biocompatibility. Suitable hydrophylic polymers include partial salts of polyacrylic acid or its derivatives. Alternatively, natural polysaccharide materials, such as karaya gum are suitable for use as adhesive conductive polymer strip 18. In the case of karaya gum, other additives such as plasticizer and salts to increase conductivity are normally mixed with the karaya gum. In preferred embodiments, the adhesive conductive polymer used is a material that does not dry out rapidly, so that the properties of polymer strip 18 do not change over a matter of a week or two, even after protective wax paper 20 has been removed from the bottom surface of electrode 10.

Adhesive conductive polymer strip 18 also provides some adhesion to the skin of the patient. This ensures intimate contact between polymer strip 18 and the patient's skin, thus eliminating the danger of hot spots. This also ensures that adhesive conductive polymer strip 18 will conform to the patient's skin over the entire active area of the electrode 10, even when subjected to physical movement of the patient's skin due to normal physical activity.

The attachment of the disposable electrode 10 of the present invention to the patient's skin does not, however, depend upon the adhesive properties of polymer strip 18. Instead, attachment to the patient's skin is provided by first and second adhesive regions 22 and 24, which are positioned on opposite sides of strip 18. The adhesive properties of foam tape 12 are greater than the adhesive properties of polymer strip 18. As a result, the electrical conductivity properties of polymer strip 18 need not be sacrificed in order to provide sufficient adhesion to hold the disposable electrode in place on the patient's skin. The electrical properties of polymer strip 18 are selected to provide excellent, uniform, low impedance contact with the patient's skin, with enough adhesion to maintain intimate contact with the patient's skin. Snap connector 16, conductive sheet 14, and conductive adhesive polymer strip 18 combine together to provide both uniform current density and structural integrity.

The present invention, therefore, avoids the problems encountered with prior art self-adhesive disposable electrodes. In these prior art electrodes, the adhesive conductor material has been either excessively aggressive and tends to debride the patient's skin, or has been nontacky and tends to fall off. The combination of uniform consistent high conductivity over a large area and a sufficiently adhesive surface to physically hold the electrode in place on the patient's skin has proved to be extremely difficult to achieve. Typically, either the conductive properties or the adhesive properties of the prior art self-adhesive electrodes have suffered. The present invention avoids this problem, by providing nonconductive adhesive tape 12 which provides structural support for electrode 10, and also provides the adhesive properties required to hold the entire electrode structure in place.

In the preferred embodiment shown in FIGS. 1–4, adhesive conductive strip 18 has a width of about 23.0 millimeters, a length of about 40.0 millimeters, and a thickness of about 0.8 millimeters.

As shown in FIGS. 1–4, protective wax paper 20 underlies disposable electrode 10, and adheres to bottom surface 12A of adhesive tape 12 as well as bottom surface 18A of adhesive conductive polymer strip 18. Protective wax paper 20 protects electrode 10 during storage from possible contamination, and also prevents electrode 10 from adhering to undesirable surfaces during storage. In the embodiment shown in FIGS. 1–4, wax paper 20 preferably has a width which is about 50.0 millimeters, so that there are exposed portions of wax paper 20 on either side of tape 12. This makes it very easy for the patient to remove disposable electrode 10 from wax paper 20 or vice versa.

The disposable electrode 10 of the present invention, as shown in FIGS. 1–4, is a rugged integral structure which is very inexpensive and is simple to manufacture. As can be seen from FIGS. 1–4, adhesive tape 12, conductive sheet 14, adhesive conductive polymer strip 18, and protective wax paper sheet 20 are all aligned along a common longitudinal axis and are overlayed in a laminated fashion. This structure is particularly well suited to large scale manufacturing, since adhesive tape 12, conductive sheet 14, conductive strip 18 and wax paper sheet 20 can all be formed from long continuous webs which are sequentially laminated, and then severed to form individual electrodes. The connection of electrical connector 16 is also well suited to large scale manufacturing, since connector 16 can be attached to the webs at spaced locations by a conventional snap fastener forming apparatus.

Figure 5:
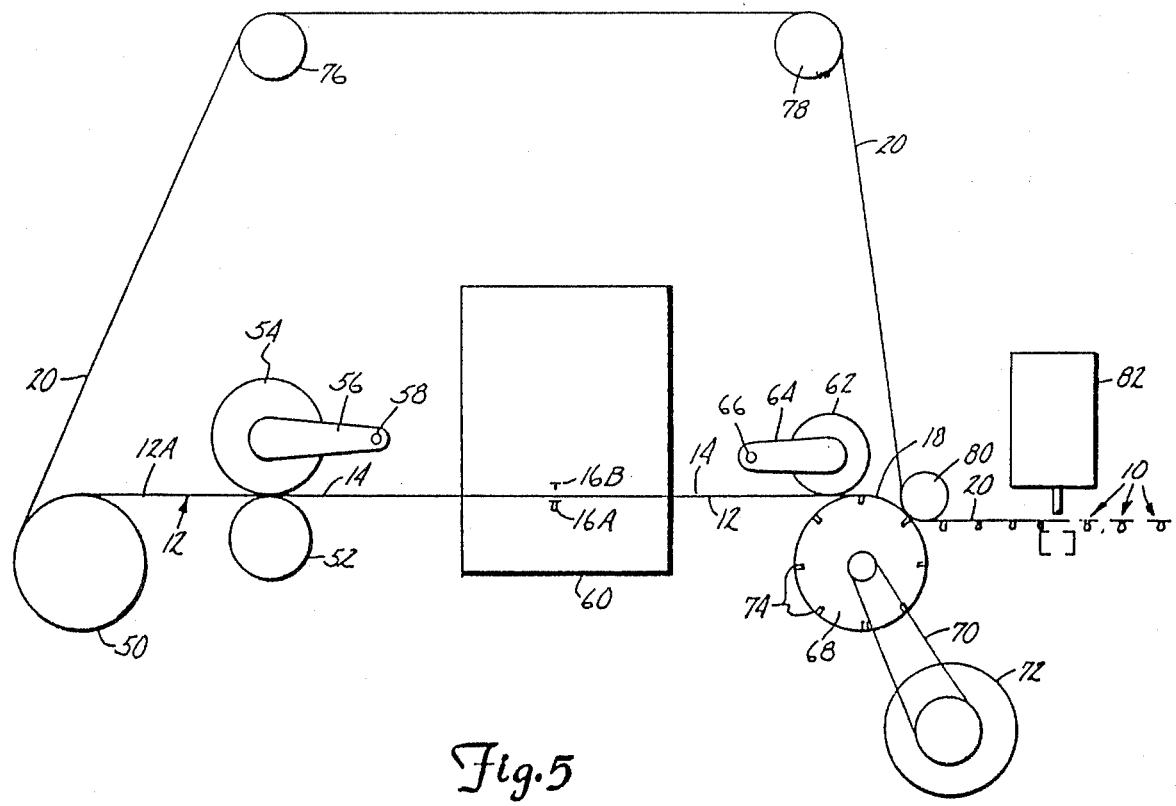
FIG. 5 is an illustration, in partially schematic form, of an apparatus and method for manufacturing the disposable electrode of the present invention.

FIG. 5 illustrates a method and apparatus for manufacturing the disposable electrode of the present invention. As shown in FIG. 5, tape 12 and wax paper 20 are initially wound on a roll 50. Adhesive tape 12 and wax paper 20 are in the form of long webs of material, with wax paper sheet 20 in contact with adhesive surface 12A of tape web 12. As tape web 12 is withdrawn from roll 50, wax paper web 20 is separated from adhesive surface 12A. Tape 12 is advanced in stepwise fashion along a generally horizontal path in increments which are equal in length to the spacing between connectors 16 of individual adjacent electrodes 10.

Adhesive tape web 12 passes between a lower idler roller 52 and roll 54, which is a wound roll containing a web of conductive foil 14. Foil roll 54 is mounted for rotation at one end of arm 56. The opposite end of arm 56 is pivoted about horizontal pivot axis 58, so that gravity forces roll 54 downward into contact with adhesive surface 12A of tape web 12. As a result, foil web 14 is brought into contact with adhesive surface 12A and is withdrawn from roll 54 as tape web 12 is advanced. As is illustrated in FIGS. 1–4, the width of tape web 12 is greater than the width of foil web 14, so that adhesive regions 22 and 24 of tape web 12 remain exposed.

The next station along the horizontal path is a snap connector mounting station. Automatic feed and rivet machine 60 is located at this station, and mounts snap connector 16 on the composite web formed by tape web 12 and metal foil web 14. In the embodiments shown in FIG. 5, metal foil web 14 is on top. Rivet machine 60 inserts bottom part 16B downward through webs 14 and 12 and mounts top part 16A on stud 28 of lower part 16B which projects downward below tape web 12. Once snap connector 16 has been mounted on the composite web, rivet machine 60 advances the composite web by the predetermined feed length, which is equal to the spacing between connectors 16 of adjacent electrodes being formed from the composite web.

Adhesive conductive hydrophylic polymer 18 is a web supplied from roll 62, which is rotatably mounted at one end of arm 64. Arm 64 is pivotally mounted for rotation about horizontal pivot axis 66 so that polymer web 18 is brought into contact with foil web 14. The adhesive properties of polymer web 18 cause it to adhere to foil web 14. In addition, in one preferred embodiment the width of polymer web 18 is slightly larger than the width of foil web 14, so that polymer web 18 slightly overlaps web foil 14 and comes into contact with portions of the adhesive surface 12A of tape 12.

The composite web is advanced in stepwise fashion by advance drive wheel 68, which is driven through drive belt 70 by motor 72. Advance drive wheel 68 has indentations 74 at spaced locations around its periphery for receiving and engaging the upper part 16A of snap connector 16 which projects below the composite web. This allows advance drive wheel 68 to apply force to the composite web.

Protective wax paper web 20, which was separated from adhesive tape web 12, passes over idler rollers 76 and 78 and then under idler roller 80, where wax paper web 20 is brought into contact with adhesive surface 12A of tape 12 and adhesive surface 18A of conductive polymer 18.

Cutting unit 82 severs individual electrodes 10 from the composite web. In one preferred embodiment of the present invention, cutting unit 82 is a pneumatically actuated cutter which is actuated after each advance cycle of the composite web.

In another embodiment of the present invention, cutting unit 82 cuts through all layers of the composite electrode except for wax paper 20. This allows many disposable electrodes to be packaged on a single wax paper backing sheet.

In conclusion, the disposable electrode of the present invention is very inexpensive, is simple to manufacture, and yet is easy and safe to use by a patient without the assistance of medical personnel. The low cost of individual electrodes and the ability to manufacture electrodes of the present invention on a large scale production basis makes the present invention particularly well suited as a disposable stimulating electrode, which can be discarded after a single use.

Although the present invention has been described with reference to preferred embodiments, workers skilled in the art will recognize that changes may be made in form and detail without departing from the spirit and scope of the invention.

What is claimed is:

1. A method of fabricating an integral disposable electrode for establishing a low impedance electrical connection to a patient's skin, the method comprising:

providing a first web of flexible electrically nonconductive adhesive tape having a first nonadhesive major surface and a second adhesive major surface, the first web having a first width;

providing a second web of flexible electrically conductive sheet material having first and second major surfaces, the second web having a second width which is less than the first width;

providing a third web of flexible biocompatible electrically conductive adhesive polymer material, the third web having first and second adhesive major surfaces and having a third width which is at least essentially equal to the second width and which is less than the first width;

providing a fourth web of nonadhesive protective material having first and second major surfaces and having a fourth width which is at least essentially equal to the first width;

laminating the first, second, third and fourth webs to form a composite web with the second adhesive major surface of the first web in contact with and adhered to the first major surface of the second web, with the second major surface of the second web in contact with and adhered to first adhesive major surface of the third web, and with the first major surface of the fourth web in contact with the second adhesive major surface of the third web and in contact with portions of the second adhesive major surface of the first web positioned on opposite sides of the third web;

attaching electrical terminals to the second web at spaced longitudinal locations; and severing the first, second and third webs of the laminated composite web in a transverse direction at positions between adjacent spaced electrical terminals to define individual integral disposable electrodes.

2. The method of claim 1 wherein the electrical terminals are electrically conductive snap connectors.

3. The method of claim 1 wherein the fourth web has a fourth width which is greater than the first width.

* * * * *